United States Patent
Olek et al.

(10) Patent No.: US 7,405,040 B2
(45) Date of Patent: Jul. 29, 2008

(54) LIGASE/POLYMERASE METHOD FOR DETECTING CYTOSINE METHYLATION IN DNA SAMPLES

(75) Inventors: Alexander Olek, Berlin (DE); Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 430 days.

(21) Appl. No.: 10/204,961

(22) PCT Filed: Feb. 23, 2001

(86) PCT No.: PCT/DE01/00749

§ 371 (c)(1),
(2), (4) Date: Dec. 30, 2002

(87) PCT Pub. No.: WO01/62961

PCT Pub. Date: Aug. 30, 2001

(65) Prior Publication Data

US 2003/0119025 A1  Jun. 26, 2003

(30) Foreign Application Priority Data

Feb. 25, 2000  (DE)  ................. 100 10 281

(51) Int. Cl.
*C12Q 1/68* (2006.01)
*C07H 21/04* (2006.01)

(52) U.S. Cl. ............ 435/6; 536/24.31; 536/24.32; 536/24.33

(58) Field of Classification Search ............ 435/6, 435/91.2; 536/23.1, 24.31, 24.32, 24.33
See application file for complete search history.

(56) References Cited

U.S. PATENT DOCUMENTS

| | | | | |
|---|---|---|---|---|
| 4,988,617 A | * | 1/1991 | Landegren et al. ............ 435/6 |
| 5,679,524 A | * | 10/1997 | Nikiforov et al. ............ 435/6 |
| 5,728,526 A | | 3/1998 | George, Jr. et al. | |
| 6,013,431 A | | 1/2000 | Soderlund et al. | |
| 6,027,889 A | * | 2/2000 | Barany et al. ............ 435/6 |
| 6,214,556 B1 | * | 4/2001 | Olek et al. ............ 435/6 |
| 7,118,868 B2 | * | 10/2006 | Berlin ............ 435/6 |
| 2003/0129620 A1 | * | 7/2003 | Olek et al. ............ 435/6 |

FOREIGN PATENT DOCUMENTS

| WO | WO 95/21271 | 8/1995 |
|---|---|---|
| WO | WO 99/28498 | 6/1999 |
| WO | WO 99/67414 A1 | 12/1999 |

OTHER PUBLICATIONS

Grunau et al., "Bisulfite genomic sequencing: systematic investigation of critical experimental parameters," Nucleic Acids Research, 29(13):e65 (2001).
Oakeley, "DNA methylation analysis: a review of current technologies," Pharmacology & Therapeutics, 84:389-400 (1999).
Gonzalgo et al., Nucleic Acids Research, 25(12):2529-31 (1997).
Xiong et al., Nucleic Acids Research, 25(12):2532-4 (1997).
Grigg et al., BioEssays, 16(6):431-6 (1994).

* cited by examiner

*Primary Examiner*—Suryaprabha Chunduru
(74) *Attorney, Agent, or Firm*—Kriegsman & Kriegsman

(57) ABSTRACT

Described is a method for detecting 5-methylcytosine in genomic DNA samples. First, a genomic DNA from a DNA sample is chemically converted with a reagent, 5-methylcytosine and cytosine reacting differently, and the pretreated DNA is subsequently amplified using a polymerase and at least one primer. In the next step, the amplified genomic DNA is hybridized to at least two oligonucleotides, the latter being joined by inserting at least one oligonucleotide. In the ligation product, one nucleotide carries a detectable label, and the elongation depends on the methylation status of the specific cytosine in the genomic DNA sample. In the next step, the elongated oligonucleotides are analyzed for the presence of the label.

38 Claims, No Drawings

SEQUENCE LISTING

```
<160> NUMBER OF SEQ ID NOS: 7

<210> SEQ ID NO 1
<211> LENGTH: 31
<212> TYPE: DNA
<213> ORGANISM: artificial sequence
<220> FEATURE:
<223> OTHER INFORMATION: oligonucleotide

<400> SEQUENCE: 1
attatgttgg agtagtagag tttaaatggt t                              31

<210> SEQ ID NO 2
<211> LENGTH: 32
<212> TYPE: DNA
<213> ORGANISM: artificial sequence
<220> FEATURE:
<223> OTHER INFORMATION: oligonucleotide

<400> SEQUENCE: 2
acttaacact tactatttaa atcacaaccc at                             32

<210> SEQ ID NO 3
<211> LENGTH: 18
<212> TYPE: DNA
<213> ORGANISM: artificial sequence
<220> FEATURE:
<223> OTHER INFORMATION: oligonucleotide

<400> SEQUENCE: 3
atgttggatg ttgttgag                                             18

<210> SEQ ID NO 4
<211> LENGTH: 25
<212> TYPE: DNA
<213> ORGANISM: artificial sequence
<220> FEATURE:
<223> OTHER INFORMATION: oligonucleotide

<400> SEQUENCE: 4
gtataaagta aattagaagg aagat                                     25
```

```
<210> SEQ ID NO 5
<211> LENGTH: 22
<212> TYPE: DNA
<213> ORGANISM: artificial sequence
<220> FEATURE:
<223> OTHER INFORMATION: oligonucleotide

<400> SEQUENCE: 5
atgttggatg ttgttgagaa ac                                        22

<210> SEQ ID NO 6
<211> LENGTH: 22
<212> TYPE: DNA
<213> ORGANISM: artificial sequence
<220> FEATURE:
<223> OTHER INFORMATION: oligonucleotide

<400> SEQUENCE: 6
atgttggatg ttgttgagaa at                                        22

<210> SEQ ID NO 7
<211> LENGTH: 47
<212> TYPE: DNA
<213> ORGANISM: artificial sequence
<220> FEATURE:
<223> OTHER INFORMATION: oligonucleotide

<400> SEQUENCE: 7
atgttggatg ttgttgagaa atgtataaag taaattagaa ggaagat             47
```

LIGASE/POLYMERASE METHOD FOR DETECTING CYTOSINE METHYLATION IN DNA SAMPLES

BACKGROUND OF THE INVENTION

The present invention relates to a method for detecting 5-methylcytosine in genomic DNA-samples.

The levels of observation that have been well studied by the methodological developments of recent years in molecular biology are the genes themselves, the translation of these genes into RNA, and the resulting proteins. The question of which gene is switched on at which point in the course of the development of an individual, and how the activation and inhibition of specific genes in specific cells and tissues are controlled is correlatable to the degree and character of the methylation of the genes or of the genome. In this respect, the assumption suggests itself that pathogenic conditions express themselves in an altered methylation pattern of individual genes or of the genome.

The present invention describes a method for detecting the methylation state of genomic DNA samples. The method can, at the same time, also be used for detecting point mutations and single nucleotide polymorphisms (SNPs).

5-methylcytosine is the most frequent covalently modified base in the DNA of eukaryotic cells. It plays a role, for example, in the regulation of transcription, in genetic imprinting, and in tumorgenesis. Therefore, the identification of 5-methylcytosine as a component of genetic information is of considerable interest. However, 5-methylcytosine positions cannot be identified by sequencing since 5-methylcytosine has the same base pairing behavior as cytosine. Moreover, the epigenetic information carried by the 5-methylcytosines is completely lost during PCR amplification.

A relatively new, and currently the most frequently used method for analyzing DNA for 5-methylcytosine is based on the specific reaction of bisulfite with cytosine which, upon subsequent alkaline hydrolysis, is converted into uracil which corresponds to thymidine in its base pairing behavior. However, 5-methylcytosine remains unmodified under these conditions. Consequently, the original DNA is converted in such a manner that methylcytosine, which originally could not be distinguished from cytosine by its hybridization behavior, can now be detected as the only remaining cytosine using "normal" molecular biological techniques, for example, by amplification and hybridization or sequencing. All of these techniques are based on base pairing which can now be fully exploited. In terms of sensitivity the prior art is defined by a method which encloses the DNA to be analyzed in an agarose matrix, thus preventing the diffusion and renaturation of the DNA (bisulfite only reacts with single-stranded DNA), and which replaces all precipitation and purification steps with fast dialysis (Olek, A. et al, Nucl. Acids. Res. 1996, 24, 5064-5066). Using this method, it is possible to analyze individual cells, which illustrates the potential of the method. Until now, however, only individual regions of a length of up to approximately 3000 base pairs are analyzed; a global analysis of cells for thousands of possible methylation analyses is not possible. Moreover, this method cannot reliably analyze very small fragments from small sample quantities either. These are lost in spite of the diffusion protection by the matrix.

An overview of further methods of detecting 5-methylcytosines can be gathered from the following survey article: Rein, T., DePamphilis, M. L., Zorbas, H., Nucleic Acids Res. 1998, 26, 2255., With few exceptions (e.g., Zeschnigk M. et al, Eur. J. Hum. Genet. 1997, 5, 94-98), the bisulfite technology is currently only used in research. Always, however, short specific fragments of a known gene are amplified subsequent to a bisulfite treatment and either completely sequenced (Olek, A. and Walter, J., Nat. Genet. 1997, 17, 275-276) or individual cytosine positions are detected by a primer extension reaction (Gonzalgo, M. L., and Jones, P. A., Nucl. Acids Res. 1997, 25, 2529-2531, WO Patent 9500669) or by enzymatic digestion (Xiong, Z. and Laird, P. W., Nucl. Acids. Res. 1997, 25, 2532-2534). In addition, detection by hybridization has also been described (Olek et al., WO 99 28498).

Further publications dealing with the use of the bisulfite technique for methylation detection in individual genes are: Xiong, Z. and Laird, P. W. (1997), Nucl. Acids Res. 25, 2532; Gonzalgo, M. L. and Jones, P. A. (1997), Nucl. Acids Res. 25, 2529; Grigg, S. and Clark, S. (1994), Bioassays 16, 431; Zeschnik, M. et al. (1997), Human Molecular Genetics 6, 387; Teil, R. et al. (1994), Nucl. Acids Res. 22, 695; Martin, V. et al. (1995), Gene 157, 261; WO 97 46705, WO 95 15373 and WO 45560.

An overview of the Prior Art in oligomer array manufacturing can be gathered from a special edition of Nature Genetics (Nature Genetics Supplement, Volume 21, January 1999), published in January 1999, and from the literature cited there.

There are different methods known for immobilizing DNA. The best-known method is the fixed binding of a DNA which has been functionalized with biotin to a streptavidin-coated surface (Uhlen, M. et al. 1988, Nucleic Acids Res. 16, 3025-3038). The binding strength of this system corresponds to that of a covalent chemical bond without being one. To be able to covalently bind a target DNA to a chemically prepared surface, a corresponding functionality of the target DNA is required. DNA itself does not possess any functionalization which is suitable. There are different variants of introducing a suitable functionalization into a target DNA: two functionalizations which are easy to handle are primary aliphatic amines and thiols. Such amines are quantitatively converted with N-hydroxysuccinimide esters, and thiols react quantitatively with alkyl iodides under suitable conditions. The difficulty exists in introducing such a functionalization into a DNA. The simplest variant is the introduction via a PCR primer in a PCR. Disclosed variants use 5'-modified primers ($NH_2$ and SH) and a bifunctional linker.

An essential component of the immobilization on a surface is its constitution. Systems described heretofore are mainly composed of silicon or metal. A further method of binding a target DNA is based on the use of a short recognition sequence (e.g., 20 bases) in the target DNA for hybridization to a surface-immobilized oligonucleotide. Enzymatic variants for introducing chemically activated positions in a target DNA have been described as well. In this case, a 5'-$NH_2$-functionalization is carried out enzymatically on a target DNA.

For scanning an immobilized DNA array, fluorescently labeled probes have often been used. Particularly suitable for fluorescence labeling is the simple attachment of Cy3 and Cy5 dyes to the 5'-OH of the specific probe. The detection of the fluorescence of the hybridized probes is carried out, for example via a confocal microscope. Cy3 and Cy5 dyes, besides many others, are commercially available.

An overview of the Prior Art in oligomer array manufacturing can be gathered from a special edition of Nature Genetics (Nature Genetics Supplement, Volume 21, January 1999), published in January 1999, and from the literature cited there, as well as from U.S. Pat. No. 5,994,065 on methods for preparing solid supports for target molecules such a oligonucleotides at reduced, non-specific background signal.

More recent methods for detecting mutations are specified in the following:

Worth mentioning as a special case of sequencing is the single-base primer extension (Genetic Bit Analysis) (Head, S R., Rogers, Y H., Parikh K., Lan, G., Anderson, S., Goelet, P., Boycejacino M T., Nucleic Acids Research. 25(24): 5065-5071, 1997; Picoult-Newberg, L., Genome Res. 9(2): 167-174, 1999). A combined amplification and sequencing is described in U.S. Pat. No 5,928,906 where a base-specific termination on matrix molecules is used. A further method uses a ligase/polymerase reaction for identifying nucleotides (U.S. Pat. No. 5,952,174).

Matrix Assisted Laser Desorption Ionization Mass Spectrometry (MALDI) is a very efficient development for the analysis of biomolecules (Karas, M. and Hillenkamp, F. (1988), Laser desorption ionization of proteins with molecular masses exceeding 10000 daltons. Anal. Chem. 60: 2299-2301). An analyte is embedded in a light-absorbing matrix. Using a short laser pulse, the matrix is evaporated, thus transporting the analyte molecule into the vapor phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than larger ones.

MALDI is ideally suited to the analysis of peptides and proteins. The analysis of nucleic acids is somewhat more difficult (Gut, I. G. and Beck, S. (1995), DNA and Matrix Assisted Laser Desorption Ionization Mass Spectrometry. Molecular Biology: Current Innovations and Future Trends 1: 147-157.). The sensitivity for nucleic acids is approximately 100 times worse than for peptides and decreases disproportionally with increasing fragment size. For nucleic acids having a multiply negatively charged backbone, the ionization process via the matrix is considerably less efficient. For MALDI, the selection of the matrix plays an eminently important role. For the desorption of peptides, several very efficient matrixes have been found which produce a very fine crystallization. For DNA, there are currently several responsive matrixes in use, however, this has not reduced the difference in sensitivity. The difference in sensitivity can be reduced by chemically modifying the DNA in such a manner that it becomes more similar to a peptide. Phosphorothioate nucleic acids in which the usual phosphates of the backbone are substituted by thiophosphates can be converted into a charge-neutral DNA using simple alkylation chemistry (Gut, I. G. and Beck, S. (1995), A procedure for selective DNA alkylation and detection by mass spectrometry. Nucleic Acids Res. 23: 1367-1373). The coupling of a charge tag to this modified DNA results in an increase in sensitivity to the same amount as that found for peptides. A further advantage of charge tagging is the increased stability of the analysis against impurities which make the detection of unmodified substrates considerably more difficult.

Genomic DNA is obtained from DNA of cell, tissue or other test samples using standard methods. This standard methodology is found in references such as Fritsch and Maniatis eds., Molecular Cloning: A Laboratory Manual, 1989.

Mutualities between promoters consist not only in the occurrence of TATA- or GC-boxes but also for which transcription factors they possess binding sites and at what distance these are located from each other. The existing binding sites for a specific protein do not match completely in their sequence but conserved sequences of at least 4 bases are found which can still be elongated by inserting wobbles, i.e., positions at which in each case different bases are located. Moreover, these binding sites are present at specific distances from each other.

However, the distribution of the DNA in the interphase chromatin which occupies the largest portion of the nuclear volume is subject to a very special arrangement. Thus, the DNA is attached to the nuclear matrix, a filamentous pattern at the inner side of the nuclear membrane, at several locations. These regions are designated as matrix attachment regions (MAR) or scaffold attachment regions (SAR). The attachment has an essential influence on the transcription or the replication. These MAR fragments have no conserved sequences, but to 70% they consist of A or T, and are located in the vicinity of cisacting regions, which regulate the transcription in a general manner, and in the vicinity of topoisomerase II recognition sites.

In addition to promoters and enhancers, further regulatory elements, so-called "insulators", exist for different genes. These insulators can, for example, inhibit the action of the enhancer on the promotor if they are located between enhancer and promotor, or else, if located between heterochromatin and a gene, can protect the active gene from the influence of the heterochromatin. Examples of such insulators include: firstly, so-called "LCR" (locus control regions) consisting of several sites which are hypersensitive to DNAase I; secondly, certain sequences such as SCS (specialized chromatin structures) or SCS', 350 or 200 bp long, respectively, and highly resistant to degradation by DNAase I, and flanked on both sides with hypersensitive sites (distance in each case 100 bp). The protein BEAF-32 binds to scs'. These insulators can be located on both sides of the gene.

SUMMARY OF THE INVENTION

It is the aim of the present invention to provide a method particularly suitable for concurrently detecting cytosine methylations and SNPs in genomic DNA samples. In the process, it should preferably be possible for a plurality of fragments to be analyzed concurrently.

According to the invention the aim is reached by a method for detecting 5-methylcytosine in genomic DNA samples, wherein the following steps are carried out:

(a) a genomic DNA from a DNA sample is chemically converted with a reagent, 5-methylcytosine and cytosine reacting differently, thus exhibiting a different base pairing behavior in the DNA duplex subsequent to the reaction;

(b) the pretreated DNA is amplified using a polymerase and at least one oligonucleotide (type A) as a primer;

(c) a set of oligonucleotides is hybridized to the amplified genomic DNA, forming a duplex; this set of oligonucleotides consisting of different species of type B and of type C; and said hybridized oligonucleotides of type B, with their 3'-ends, immediately or at a distance of up to 10 bases, adjoining the positions to be analyzed with regard to their methylation in the genomic DNA sample; and said second oligonucleotide (type C) hybridizing to a second region of the target molecule so that the 5'-end of the second oligonucleotide (type C) is separated from the 3'-end of the first oligonucleotide (type B) at the location of said selected position by a gap of the size of a single nucleotide or of up to 10 nucleotides;

(d) the oligonucleotide (type B) having a known sequence of n nucleotides is elongated by means of a polymerase by not more than the number of nucleotides lying between the 3'-end of the oligonucleotide of type B and the 5'-end of the oligonucleotide of type C, the elongation depending on the methylation status of the specific cytosine in the genomic DNA sample;

(e) the oligonucleotides are incubated in the presence of a ligase, the adjoining first oligonucleotide of type B elongated by the polymerase reaction and the second oligonucleotide of type C being linked, resulting in a ligation product provided that the oligonucleotide of type B has been elongated in the preceding step in such a manner that now the 3'-end with existing 3'-hydroxy function immediately adjoins the 5'-end of the oligonucleotide of type C;

(f) it is detected whether a ligation product has formed.

Herein, according to the present invention it is preferred that the 5'-end of the first oligonucleotide (type B) is immobilized to a solid phase or that the 3'-end of the second oligonucleotide (type C) is immobilized to a solid phase.

According to the invention it is further preferred that the amplificates produced in step b are bonded to a solid phase at defined locations. Herein it is particularly preferred that at least one primer (type A) is bonded to a solid phase during amplification.

It is furthermore preferred that different amplificates are arranged on the solid phase in the form of a rectangular or hexagonal lattice.

It is further preferred that different oligonucleotide sequences are arranged on a plane solid phase in the form of a rectangular or hexagonal lattice.

It is also preferred that the labels attached to the elongated oligonucleotides are identifiable at each position of the solid phase at which an oligonucleotide sequence is located.

According to the present invention it is further preferred that the solid phase surface is composed of silicon, glass, polystyrene, aluminum, steel, iron, copper, nickel, silver, or gold.

It is particularly preferred that, prior to the amplification, the treatment of the the DNA using a bisulfite solution (=disulfite, hydrogen sulfite) is carried out.

According to the invention it is also preferred that the amplification is carried out by means of the polymerase chain reaction (PCR).

It is further preferred that the oligonucleotides of type A used either contain only the bases T, A and C or else the bases T, A und G and/or the oligonucleotides of type B and/or C used either contain only the bases T, A and C or else the bases T, A und G.

It is particularly preferred that the ligation products and/or the elongation products are provided with a detectable label for detection. Whereby it is particularly preferred that the labels are fluorescence labels or that the labels are radionuclides or that the labels are detachable mass labels which are detectable in a mass spectrometer.

It is preferred herein that the elongated oligonucleotides and ligation products altogether are detectable in the mass spectrometer, thus being uniquely labeled by their masses. According to the present invention it is further preferred that in each case one fragment of the elongated and/or ligated oligonucleotides is detectable in the mass spectrometer.

According to the method of the invention it is furthermore preferred that the fragment is produced by digestion with one or several exo- or endonucleases.

Herein it is particularly preferred that the produced fragments have a single positive or negative net charge for better detectability in the mass spectrometer.

Within the method of the invention it is furthermore preferred according to the invention that the detection of the elongated oligonucleotides and/or of the ligation products is carried out and visualized by means of matrix assisted laser desorption/ionization mass spectrometry (MALDI) or using electron spray mass spectrometry (ESI).

A method wherein the polymerases are heat-resistant DNA-polymerases and/or the ligases are thermostable ligases is also preferred.

A method wherein SNPs are also detected and visualized in addition to the DNA methylation is further preferred.

A method is preferred wherein the used nucleotides are terminating (type D 2) and/or chain-elongating nucleotides (type D 1). It is particularly preferred that the chain-terminating nucleotide (type D 2) is selected from a group containing either the bases T and C or else the bases G and A and/or the chain-elongating nucleotides (type D 1) are selected from a group containing either the nucleobases A, T and C or else the bases G and A and T.

It is further preferred that the fluorescently labeled dCTP-derivate is Cy3-dCTP or Cy5-dCTP.

According to the present invention it is also preferred that the amplification of several DNA segments is carried out in one reaction vessel.

Particularly preferred is the method according to the invention, wherein in step a) the genomic DNA was obtained from a DNA sample, sources of DNA comprising, e.g., cell lines, blood, sputum, stool, urine, cerebral-spinal fluid, tissue embedded in paraffin, histologic object slides, and all possible combinations thereof.

According to the invention it is further preferred that the 3'-end of the oligonucleotide of type B elongated in step d is formed by the nucleotide 2'-desoxyadenosine which, through its 3'-hydroxy function, enables the ligation in step e, whereas a 2',3'-didesoxyguanosine at the 3'-end of the oligonucleotide does not give rise to a ligation product and/or that the 3'-end of the oligonucleotide of type B elongated in step d is formed by the nucleotide 2'-desoxyguanosine which, through its 3'-hydroxy function, enables the ligation in step e, whereas a 2',3'-didesoxyadenosine at the 3'-end of the oligonucleotide does not give rise to a ligation product and/or that the 3'-end of the oligonucleotide of type B elongated in step d is formed by the nucleotide thymidine which, through its 3'-hydroxy function, enables the ligation in step e, whereas a 2',3'-didesoxycytidine at the 3'-end of the oligonucleotide does not give rise to a ligation product and/or that the 3'-end of the oligonucleotide of type B elongated in step d is formed by the nucleotide 2'-desoxycytidine which, through its 3'-hydroxy function, enables the ligation in step e, whereas a 2',3'-didesoxythymidine at the 3'-end of the oligonucleotide does not give rise to a ligation product.

According to the invention it is furthermore preferred that the methylation analyses of the upper and lower DNA strands are carried out concurrently.

Finally a method according to the present invention is preferred, wherein the steps c-e are carried out in solution and the ligated oligonucleotides are applied to a solid phase for the detection.

DETAILED DESCRIPTION OF THE INVENTION

Described is a method for detecting methylcytosine in genomic DNA samples:

The method includes the amplification, hybridization and elongation reaction of an entire DNA or of a fragment thereof. The method can be used for detecting methylcytosine and, at the same time, also of single nucleotide polymorphisms (SNPs) and mutations.

The genomic DNA to be analyzed is preferably obtained from usual sources of DNA such as cell lines, blood, sputum, stool, urine, cerebral-spinal fluid, tissue embedded in paraffin, histologic object slides, and all possible combinations thereof.

In the first step of the method, the DNA used is preferably treated with bisulfite (=disulfite, hydrogen sulfite) or else with another chemical in such a manner that all cytosine bases which are not methylated at the 5-position of the base are changed in such a manner that a different base results with regard to the base pairing behavior while the cytosines methylated at the 5-position remain unchanged. If bisulfite is used, then an addition takes place at the non-methylated cytosine bases. The subsequent alkaline hydrolysis then gives rise to the conversion of non-methylated cytosine nucleobases to uracil. The genomic DNA used is preferably fragmented using a restriction endonuclease prior to the chemical treatment.

In the second step of the method, the pretreated DNA is preferably amplified using a heat-resistant polymerase and at least one primer (type A). This primer may preferably contain 10-40 base pairs.

In a particularly preferred variant of the method, the amplification is carried out with primers of type A by means of the polymerase chain reaction (PCR).

In a preferred variant of the method, the amplification of several DNA fragments is carried out in one reaction vessel. This may either be a so-called multiplex PCR in which different primers each produce defined fragments. Different, defined amplifications are carried out in one reaction vessel. In a further, particularly preferred variant of the method, primers in each case selectively and reproducibly amplify several fragments. This is achieved, for example, in that the primers bind, for example, to repetitive elements in the genome. In a particularly preferred variant of the method, the primers bind to transcription factor binding sites, to promoters or other regulatory elements in genes. In a particularly preferred variant of the method, the amplification is carried out by carried out by elongating primers which are bonded to a solid phase. A multiplex PCR in the broader sense can be carried out in that different primers are bonded at different, defined locations of a solid phase. In these implementations of the amplification, the primer (e.g., forward-Primer) which in each case is complementary to a strand is always immobilized, and the primer (e.g., reverse primer) which in each case is complementary to the counter strand is present in solution.

In a further preferred variant of the second method step, the solid phase is plane, the different oligonucleotide sequences being arranged in the form of a rectangular or hexagonal lattice. The result of this is that the different amplificates are arranged on the solid phase in the form of a rectangular or hexagonal lattice, as well. In this case, as already described above, several amplificates are directly produced on the solid phase.

The solid phase surface is preferably composed of silicon, glass, polystyrene, aluminum, steel, iron, copper, nickel, silver, or gold.

In a particularly preferred variant of the method, the oligonucleotides of type A either contain only bases T, A and C or only bases T, A and G.

In the third step of the method, a set of oligonucleotides composed of two types of oligonucleotides, a first (type B) and a second (type C) oligonucleotide, is hybridized to a selected position of the amplified genomic DNA. The first oligonucleotide (type B) is a primer which hybridizes to a first region of the target sequence to be analyzed in such a manner that its 3'-end, immediately or at a distance of up to 10 bases, adjoins the positions to be analyzed with regard to their methylation in the genomic DNA sample. The second oligonucleotide (type C) hybridizes to a second region of the target molecule so that the 5'-end of the second oligonucleotide (type C) is separated from the 3'-end of the first hybridized oligonucleotide (type B) at the location of said selected position by a gap of the size of a single nucleotide or of up to 10 nucleotides.

The oligonucleotides of type B which are hybridized to the amplificates can be bonded to a solid phase with their 5'-end, or with another base, or via their backbone but not via their 3'-end. Preferably, the binding occurs via the 5'-end. In a preferred variant, the solid phase is plane, the different oligonucleotide sequences (type B) being arranged in the form of a rectangular or hexagonal lattice.

The oligonucleotides of type C which are hybridized to the amplificates can be bonded to a solid phase with their 3'-end, or at another base, or via their backbone but not via their 5'-end. Preferably, the binding occurs via the 3'-end. In a preferred variant, the solid phase is plane, the different oligonucleotide sequences (type C) being arranged in the form of a rectangular or hexagonal lattice. The 5'-end of the oligonucleotide of type C must be phosphorylated.

In summary, the following different possibilities preferably exist for the immobilization to a solid phase:
1. The 5'-end of the first oligonucleotide (type B) is immobilized to a solid phase.
2. The 3'-end of the second oligonucleotide (type C) is immobilized to a solid phase.
3. The amplification is already carried out on a solid phase; in this case, preferably the 5'-end of a primer is bonded to the solid phase.
4. The amplification, hybridization, elongation reaction and ligation are preferably carried out in solution, and then the ligation product is applied to the solid phase for detection.

The solid phase surface is preferably composed of silicon, glass, polystyrene, aluminum, steel, iron, copper, nickel, silver, or gold.

In a particularly preferred variant of the method, the oligonucleotides of type B and/or of type C either contain only bases T, A and C or only bases T, A and G.

In the fourth method step, the oligonucleotide (type B) having a known sequence of n nucleotides is elongated with a heat-resistant polymerase by not more than the number of nucleotides lying between the 3'-end of the oligonucleotide of type B and the 5'-end of the oligonucleotide of type C. In this context, preferably, at least one nucleotide carries a detectable label. In a particularly preferred variant of the method, either the oligonucleotide of type B or the oligonucleotide of type C carries a detectable label. In this context, the type of elongation depends on the methylation status of the specific cytosine in the genomic DNA sample or else on possibly existing SNPs, point mutations or deletions, insertions and inversions.

In a preferred variant of the method, the used nucleotides are terminating (type D 2) and/or chain-elongating nucleotides (type D 1). In this context, the terminating nucleotide (type D 2) is a 2',3'-didesoxynucleotide, and the chain-elongating nucleotide is a 2'-desoxynucleotide. In a particularly preferred variant of the method, the nucleobases of type D 1 are selected from a group containing bases T, A and C or else bases T, A and G. In a further, particularly preferred variant of the method, the nucleobases of type D 2 are selected from a group containing either bases T and C or bases G and A.

The labeling of the elongated oligonucleotides of type B is preferably carried out via absorbing dyes and/or via chemiluminescence and/or via radioactive isotopes and/or via fluorescence labels which are introduced via the nucleotides attached in the fourth method step or else via the oligonucleotides of types B or C. In the case that the oligonucleotides are labeled, the immobilized oligonucleotide is not labeled. Also preferred is the labeling via the molecular mass of the elongated and ligated oligonucleotide.

In the fifth method step, the hybridized oligonucleotides are incubated in the presence of a preferably thermostable ligase to link the adjoining hybridized first (type B) and second (type C) oligonucleotide, thereby obtaining a ligation product provided that the oligonucleotide has been elongated in the preceding step in such a manner that now a desoxynucleoside immediately adjoins the 5'-end of the oligonucleotide of type C.

In the sixth method step, it is detected whether a ligation product has formed. To this end, the elongated oligonucleotides are checked for the presence of a label at each position of the solid phase at which an oligonucleotide sequence is located.

In a particularly preferred variant of the method, the detection of the elongated oligonucleotides is carried out via their fluorescence. In this context, preferably, different ligation products have different fluorescence properties, which can be attained, for example by means of inserting nucleotides labeled with different dyes.

In a preferred variant of the method, fragments of the elongated oligonucleotide are produced by digestion with one or several exo- or endonucleases.

In a particularly preferred variant of the method, the labels of the nucleotides are detatchable mass labels which are detectable in a mass spectrometer.

In a particularly preferred variant of the method, detachable mass labels, the elongated oligonucleotides altogether or fragments thereof are detected and visualized on the basis of their unique mass by means of matrix assisted laser desorption/ionization mass spectrometry (MALDI-MS) or using electron spray mass spectrometry (ESI).

The fragments detected in the mass spectrometer preferably have a single positive or negative net charge.

In a particularly preferred variant of the method, SNPs (single nucleotide polymorphisms) and cytosine methylations are analyzed in one experiment.

In a particularly preferred variant of the method, the lower and the upper strand of the DNA sample is analyzed in one experiment subsequent to the chemical pretreatment to ensure an internal experimental control.

A further subject matter of the present invention is a kit containing chemicals and aids for carrying out the bisulfite reaction and/or the amplification, the hybridization, the elongation reaction and the ligase reaction and/or polymerases and/or the documentation for carrying out the method.

The following examples illustrate the invention.

EXAMPLE 1

The following example relates to a fragment of exon 23 of the factor VIII gene in which a specific CG-position is to be analyzed for methylation.

In the first step, the fragment is amplified by primers of type A, namely by ATTATGTTGGAGTAGTAGAGTTTAAATGGTT (SEQ-ID No.: 1) and ACTTAACACTTACTATTTAAATCACAACCCAT (SEQ-ID No.: 2). The amplified DNA is hybridized to an oligonucleotide of type B (for example, ATGTTGGATGTTGTTGAG (SEQ-ID No.: 3)) and a 5'-phosphorylated oligonucleotide of type C (for example, GTATAAAGTAAATTAGAAGGAAGAT (SEQ-ID No.: 4)). Subsequently, the elongation reaction is carried out with 2',3'-didesoxycytidine triphosphate (ddCTP, as type D 2), thymidine triphosphate (dTTP, as type D 1) and 2'-desoxyadenosine triphosphate (dATP, as type D 1). If a methylated cytosine was present, the elongation product ATGTTGGATGTTGTTGAGAAAC (SEQ-ID No.: 5) is produced which does not carry any hydroxy function at the 3'-end whereas the elongation product ATGTTGGATGTTGTTGAGAAAT (SEQ-ID No.: 6) having a 3'-OH function is produced if a nonmethylated cytosine is present in the sequence to be analyzed. In the now following ligation reaction, therefore, only the ligation product ATGTTGGATGTTGTTGAGAAAT GTATAAAGTAAATTAGAAGGAAGAT (SEQ-ID No.: 7) can be produced. Now if the oligonucleotide of type C GTATAAAGTAAATTAGAAGGAAGAT (SEQ-ID No.: 4) is fluorescently labeled, then a fluorescent label is inserted only if a non-methylated cytosine was present in the DNA sample to be analyzed.

Conversely, a control can be carried out using the same sequences but with an altered set of triphosphates. If, in the elongation reaction analogously to the above example, 2',3'-didesoxythymidine triphosphate (ddTTP, as type D2), 2'-desoxycytidine triphosphate (dCTP, as type D1), and 2'-desoxyadenosine triphosphate (dATP, as type D1) are carried out, then, after the ligase reaction in contrast, a label is inserted only if a methylated cytosine was present in the DNA sample to be analyzed.

EXAMPLE 2

The following example relates to a fragment of exon 23 of the factor VIII gene in which a specific CG-position is to be analyzed for methylation.

In the first step, the fragment is amplified by primers of type A, namely by ATTATGTTGGAGTAGTAGAGTTTAAATGGTT (SEQ-ID No.: 1) and ACTTAACACTTACTATTTAAATCACAACCCAT (SEQ-ID No.: 2). The amplified DNA is hybridized with its 5'-end to an oligonucleotide of type B (for example, ATGTTGGATGTTGTTGAG (SEQ-ID No.: 3)) which is immobilized to a solid phase surface and a 5'-phosphorylated oligonucleotide of type C (for example, GTATAAAGTAAATTAGAAGGAAGAT (SEQ-ID No.: 4)). Subsequently, the elongation reaction is carried out with 2',3'-didesoxycytidine triphosphate (ddCTP, as type D 2), thymidine triphosphate (dTTP, as type D 1) and 2'-desoxyadenosine triphosphate (dATP, as type D 1). If a methylated cytosine was present, the solid phase bonded elongation product ATGTTGGATGTTGTTGAGAAAC (SEQ-ID No.: 5) is produced which does not carry any hydroxy function at the 3'-end whereas the elongation product ATGTTGGATGTTGTTGAGAAAT (SEQ-ID No.: 6) having a 3'-OH function is produced if a non-methylated cytosine is present in the sequence to be analyzed. In the now following ligation reaction, therefore, only the solid phase bonded ligation product ATGTTGGATGTTGTTGAGAAAT GTATAAAGTAAATTAGAAGGAAGAT (SEQ-ID No.: 7) can be produced. Now if the oligonucleotide of type C GTATAAAGTAAATTAGAAGGAAGAT (SEQ-ID No.: 4) is fluorescently labeled, then a fluorescent label is inserted only if a non-methylated cytosine was present in the DNA sample to be analyzed.

Conversely, a control can be carried out using the same sequences but with an altered set of triphosphates. If, analogously to the above example in the elongation reaction, 2',3'-didesoxythymidine triphosphate (ddTTP, as type D 2), 2'-desoxycytidine triphosphate (dCTP, as type D 1), and 2'-desoxyadenosine triphosphate (dATP, as type D 1) are carried out, then, after the ligase reaction in contrast, a label is inserted only if a methylated cytosine was present in the DNA sample to be analyzed.

EXAMPLE 3

The following example relates to a fragment of exon 23 of the factor VIII gene in which a specific CG-position is to be analyzed for methylation.

In the first step, the fragment is amplified by primers of type A, namely by ATTATGTTGGAGTAGTAGAGTT-TAAATGGTT (SEQ-ID No.: 1) and ACTTAACACTTAC-TATTTAAATCACAACCCAT (SEQ-ID No.: 2). The amplified DNA is hybridized to an oligonucleotide of type B (for example, ATGTTGGATGTTGTTGAG (SEQ-ID No.: 3)) and a 5'-phosphorylated oligonucleotide of type C (for example, GTATAAAGTAAATTAGAAGGAAGAT (SEQ-ID No.: 4)), the latter beeing bonded to a solid phase surface with its 3'-end. Subsequently, the elongation reaction is carried out with 2',3'-didesoxycytidine triphosphate (ddCTP, as type D2), thymidine triphosphate (dTTP, as type D1) and 2'-desoxyadenosine triphosphate (dATP, as type D1). If a methylated cytosine was present, the solid phase bonded elongation product ATGTTGGATGTTGTTGAGAAAC (SEQ-ID No.: 5) is produced which does not carry any hydroxy function at the 3'-end whereas the elongation product ATGTTGGATGTTGTTGAGAAAT (SEQ-ID No.: 6) having a 3'-OH function is produced if a non-methylated cytosine is present in the sequence to be analyzed. In the now following ligation reaction, therefore, only the solid phase bonded ligation product ATGTTGGATGTTGTTGAGAAAT GTATAAAGTAAATTAGAAGGAAGAT (SEQ-ID No.: 7) can be produced. Now if the oligonucleotide of type B ATGT-TGGATGTTGTTGAG (SEQ-ID No.: 3) is fluorescently labeled, then a fluorescent label is inserted only if a non-methylated cytosine was present in the DNA sample to be analyzed.

Conversely, a control can be carried out using the same sequences but with a different set of triphosphates. If, analogously to the above example, in the elongation reaction 2',3'-didesoxythymidine triphosphate (ddTTP, as type D2), 2'-desoxycytidine triphosphate (dCTP, as type D1), and 2'-desoxyadenosine triphosphate (dATP, as type D1) is carried out, then, after the ligase reaction conversely, a label is inserted only if a methylated cytosine was present in the DNA sample to be analyzed.

The invention claimed is:

1. A method for detecting 5-methylcytosine in at least one genomic DNA sample, characterized in that the following steps are carried out:
   (a) genomic DNA from at least one DNA sample is chemically converted with a reagent, 5-methylcytosine and cytosine reacting differently, thus exhibiting different base pairing behaviors in the DNA duplex subsequent to the reaction;
   (b) then, the pretreated DNA is amplified using a polymerase and at least one oligonucleotide (type A) as a primer;
   (c) then, at least one set of oligonucleotides is hybridized to the amplified genomic DNA, forming a duplex; one set of oligonucleotides comprising different species of type B and of type C; and said hybridized oligonucleotides of type B, with their 3'-ends, immediately or at a distance of up to 10 bases, adjoining the positions to be analyzed with regard to their methylation in the genomic DNA sample; and said second oligonucleotide (type C) hybridizing to a second region of the target molecule so that the 5'-end of the second oligonucleotide (type C) is separated from the 3'-end of the first oligonucleotide (type B) at the location of said selected position by a gap of the size of a single nucleotide or of up to 10 nucleotides;
   (d) then, the at least one oligonucleotide (type B) having a known sequence is elongated by means of a polymerase by not more than the number of nucleotides lying between the 3'-end of the oligonucleotide of type B and the 5t-end of the oligonucleotide of type C, the elongation depending on the methylation status of the specific cytosine in the genomic DNA sample;
   (e) then, the oligonucleotides are incubated in the presence of a ligase, the adjoining first oligonucleotide of type B elongated by the polymerase reaction and the second oligonucleotide of type C being linked, resulting in a ligation product provided that the oligonucleotide of type B has been elongated in the preceding step in such a manner that now the 3'-end with existing 3'-hydroxy function immediately adjoins the 5'-end of the oligonucleotide of type C;
   (f) then, it is detected whether a ligation product has formed for each analyzed position.

2. The method as recited in claim 1, characterized in that the 5'-end of the first oligonucleotide (type B) is immobilized to a solid phase.

3. The method as recited in claim 1, characterized in that the 3'-end of the second oligonucleotide (type C) is immobilized to a solid phase.

4. The method as recited in claim 1, characterized in that the amplificates produced in step b are bonded to a solid phase at defined locations.

5. The method as recited in claim 4, characterized in that at least one primer (type A) is bonded to a solid phase during amplification.

6. The method as recited in claim 1, characterized in that different amplificates are arranged on the solid phase in the form of a rectangular or hexagonal lattice.

7. The method as recited in claim 2, characterized in that different oligonucleotide sequences are arranged on a plane solid phase in the form of a rectangular or hexagonal lattice.

8. The method as recited in claim 2, characterized in that the labels attached to the elongated oligonucleotides are identifiable at each position of the solid phase at which an oligonucleotide sequence is located.

9. The method as recited in claim 2, characterized in that solid phase surface is composed of silicon, glass, polystyrene, aluminum, steel, iron, copper, nickel, silver, or gold.

10. The method as recited in claim 1, characterized in that, prior to the amplification, the DNA is treated with a bisulfite solution.

11. The method as recited in claim 1, characterized in that the amplification is carried out by means of the polymerase chain reaction (PCR).

12. The method as recited in claim 1, characterized in that the oligonucleotides of type A used in claim 1 either contain only the bases T, A and C or else the bases T, A and G.

13. The method as recited in claim 1, characterized in that the oligonucleotides of type B and/or C used either contain only the bases T, A and C or else the bases T, A and G.

14. The method as recited in claim 1, characterized in that the ligation products and/or the elongation products are provided with a detectable label for detection.

15. The method as recited in claim 1, characterized in that the labels are fluorescence labels.

16. The method as recited in claim 1, characterized in that the labels are radionuclides.

17. The method as recited in claim 1, characterized in that the labels are detachable mass labels which are detectable in a mass spectrometer.

18. The method as recited in claim 1, characterized in that the elongated oligonucleotides and ligation products altogether are detectable in the mass spectrometer, thus being uniquely labeled by their masses.

19. The method as recited in claim 1, characterized in that in each case one fragment of the elongated andlor ligated oligonucleotides is detectable in the mass spectrometer.

20. The method as recited in claim 19, characterized in that the fragment is produced by digestion with one or several exo- or endonucleases.

21. The method as recited in claim 19, characterized in that the produced fragments have a single positive or negative net charge for better detectability in the mass spectrometer.

22. The method as recited in claim 1, characterized in that the detection of the elongated oligonucleotides andlor of the ligation products is carried out and visualized by means of matrix assisted laser desorptionlionization mass spectrometry (MALDI) or using electron spray mass spectrometry (ESI).

23. The method as recited in claim 1, wherein the polymerases are heat-resistant DNA-polymerases and/or the ligases are thermostable ligases.

24. The method as recited in claim 1, wherein SNPs are also detected and visualized in addition to the DNA methylation.

25. The method as recited in claim 1, wherein the used nucleotides are terminating (type D 2) and/or chain-elongating nucleotides (type D 1).

26. The method as recited in claim 25, wherein the chain-terminating nucleotide (type D 2) is selected from a group containing either the bases T and C or else the bases G and A.

27. The method as recited in claim 25, wherein the chain-elongating nucleotides (type D 1) are selected from a group containing either the nucleobases A, T and C or else the bases G and A and T.

28. The method as recited in claim 15, characterized in that used nucleotide dCTP is fluorescently labeled Cy3 or Cy5.

29. The method as recited in claim 1, characterized in that the amplification of several DNA segments is carried out in one reaction vessel.

30. The method as recited in claim 1, characterized in that in step (a), the genomic DNA is obtained from a DNA sample, sources of DNA comprising cell lines, blood, sputum, stool, urine, cerebral-spinal fluid, tissue embedded in paraffin, histologic object slides, and all possible combinations thereof.

31. The method as recited in claim 1, characterized in that the 3'-end of the oligonucleotide of type B elongated in step (d) is formed by the nucleotide 2'-desoxyadenosine which, through its 3'-hydroxy function, enables the ligation in step (e), whereas a 2',3'-didesoxyguanosine at the 3'-end of the oligonucleotide does not give rise to a ligation product.

32. The method as recited in claim 1, characterized in that the 3'-end of the oligonucleotide of type B elongated in step (d) is formed by the nucleotide 2'-desoxyguanosine which, through its 3'-hydroxy function, enables the ligation in step (e), whereas a 2',3'-didesoxyadenosine at the 3'-end of the oligonucleotide does not give rise to a ligation product.

33. The method as recited in claim 1, characterized in that the 3'-end of the oligonucleotide of type B elongated in step (d) is formed by the nucleotide thymidine which, through its 3'-hydroxy function, enables the ligation in step (e), whereas a 2',3'-didesoxycytidine at the 3'-end of the oligonucleotide does not give rise to a ligation product.

34. The method as recited in claim 1, characterized in that the 3'-end of the oligonucleotide of type B elongated in step (d) is formed by the nucleotide 2'-desoxycytidine which, through its 3'-hydroxy function, enables the ligation in step (e), whereas a 2',3'-didesoxythymidine at the 3'-end of the oligonucleotide does not give rise to a ligation product.

35. The method as recited in claim 1, characterized in that the methylation analyses of the upper and lower DNA strands are carried out concurrently.

36. The method as recited in claim 1, characterized in that the steps (c)-(e) are carried out in solution and that the ligated oligonucleotides are applied to a solid phase for the detection.

37. A method for detecting 5-methylcytosine in at least one genomic DNA sample, said method comprising the steps of:
(a) chemically converting genomic DNA from at least one DNA sample with a reagent, whereby 5-methylcytosine and cytosine react differently, thus exhibiting different base pairing behaviors in the DNA duplex subsequent to the reaction;
(b) then, amplifying the pretreated DNA using a polymerase and at least one oligonucleotide (type A) as a primer;
(c) then, hybridizing at least one set of oligonucleotides to the amplified genomic DNA, forming a duplex, one set of oligonucleotides comprising different species of type B and of type C, said hybridized oligonucleotides of type B, with their 3'-ends, immediately or at a distance of up to 10 bases, adjoining the positions to be analyzed with regard to their methylation in the genomic DNA sample, said second oligonucleotide (type C) hybridizing to a second region of the target molecule so that the 5'-end of the second oligonucleotide (type C) is separated from the 3'-end of the first oligonucleotide (type B) at the location of said selected position by a gap of the size of a single nucleotide or of up to 10 nucleotides;
(d) then, elongating the at least one oligonucleotide (type B) having a known sequence by means of a polymerase by not more than the number of nucleotides lying between the 3'-end of the oligonucleotide of type B and the 5'-end of the oligonucleotide of type C, the elongation depending on the methylation status of the specific cyto sine in the genomic DNA sample;
(e) then, incubating the oligonucleotides in the presence of a ligase, the adjoining first oligonucleotide of type B elongated by the polymerase reaction and the second oligonucleotide of type C being ligated to produce a ligation product, provided that the oligonucleotide of type B has been elongated in the preceding step in such a manner that now the 3'-end with existing 3'-hydroxy function immediately adjoins the 5'-end of the oligonucleotide of type C;

(f) then, detecting whether a ligation product has formed for each analyzed position.

38. The method as claimed in claim 37 wherein the 5'-end of the second oligonucleotide (type C) is separated from the 3'-end of the first oligonucleotide (type B) at the location of said selected position by a gap of a plurality of nucleotides.

* * * * *